United States Patent [19]
Barthelemy et al.

[11] Patent Number: 4,581,358
[45] Date of Patent: Apr. 8, 1986

[54] TRIAZOLO-PYRIMIDINE DERIVATIVES, A PROCESS FOR PREPARING THEM AND THEIR THERAPEUTIC USE AS CARDIOTONICS

[75] Inventors: Géard Barthelemy, Muret; Jean N. Vallat, Toulouse; Andre Hallot, St.-Gely Du Sesc, all of France

[73] Assignee: Sanofi, S.A., Paris, France

[21] Appl. No.: 628,916

[22] Filed: Jul. 9, 1984

[30] Foreign Application Priority Data

Jul. 25, 1983 [FR] France .................. 83 12443

[51] Int. Cl.[4] .................. A61K 31/505; C07D 239/00
[52] U.S. Cl. ..................... 514/258; 544/263
[58] Field of Search .................. 544/263; 424/251

[56] References Cited

U.S. PATENT DOCUMENTS 4,209,621 6/1980 Dusza .................. 544/263

OTHER PUBLICATIONS

Taniguchi Chemical Abstracts 90:198872 k.

Primary Examiner—Donald G. Daus
Assistant Examiner—Robert Benson
Attorney, Agent, or Firm—Weiser & Stapler

[57] ABSTRACT

This invention relates to triazolo-pyrimidine derivatives corresponding to the following formula:

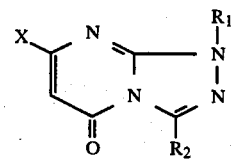

wherein

X represents a 2-pyridyl, 3-pyridyl or 4-pyridyl nucleus optionally substituted by at least one straight-chained or branched $C_{1-4}$ alkoxy or alkyl or a hydroxy or cyano group, $R_1$ represents hydrogen or a straight-chained or branched saturated or unsaturated $C_{1-5}$ aliphatic group, and $R_2$ represents a straight-chained or branched $C_{1-4}$ alkyl group, and the pharmaceutically acceptable acid addition salts thereof with inorganic or organic acids.

These compounds may be used in therapy, particularly on account of their cardiotonic activity.

14 Claims, No Drawings

TRIAZOLO-PYRIMIDINE DERIVATIVES, A PROCESS FOR PREPARING THEM AND THEIR THERAPEUTIC USE AS CARDIOTONICS

This invention relates to new triazolo-pyrimidines, a process for preparing them and their use in human and veterinary medicine.

The new compounds according to the invention correspond to the following formula:

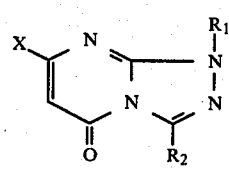

wherein

X represents a 2-pyridyl, 3-pyridyl or 4-pyridyl nucleus optionally substituted by at least one straight-chained or branched $C_{1-4}$ alkoxy or alkyl or a hydroxy or cyano group, $R_1$ represents hydrogen or a straight-chained or branched saturated or unsaturated $C_{1-5}$ aliphatic group, and $R_2$ represents a straight-chained or branched $C_{1-4}$ alkyl group, and the pharmaceutically acceptable acid addition salts thereof with inorganic or organic acids.

The invention also relates to a process for preparing the above-mentioned compounds, characterised in that a derivative of formula II:

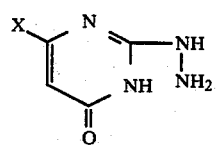

wherein X is as hereinbefore defined, is condensed with orthoesters of general formula

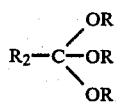

wherein $R_2$ is as hereinbefore defined and R represents a methyl or ethyl group, and subsequently, if desired, alkylation is carried out by conventional methods if it is desired to obtain compounds wherein $R_1$ is not hydrogen.

The reaction of condensation between the compounds of formulae II and III is carried out in an organic solvent. This solvent may be the orthoester itself (III) and in this case the reaction must be carried out at a temperature of 95° C. This solvent may also be xylene, butanol or toluene and the reaction may be carried out by refluxing.

The alkylation reaction is carried out by the action of an alkyl halide of formula Hal—$R_1$ where Hal represents chlorine, bromine or iodine and $R_1$ is as hereinbefore defined, in the presence of a base which may be sodium hydride or sodium amide in solvents such as dimethylformamide, dimethylsulphoxide, hexamethyl phosphotriamide, acetonitrile or toluene, at temperatures of between 25° C. and 70° C.

When $R_1$ represents a methyl or ethyl radical, the alkylating agent used may be dimethylsulphate or diethylsulphate in the presence of potassium hydroxide at temperatures of between 25° C. and 50° C. (ALLEN et al., J. Org. Chem., 25, 361, 1960).

Alkylation of these compounds may also be carried out by the action of an alkyl halide in the presence of tetrabutylammonium fluoride at ambient temperature.

The salts of the compounds of formula I are then prepared by conventional methods.

The compounds of formula II are prepared by the method described by D. LIEBERMANN and A. ROUAIX (C.R., 240, 984–986, 1955) and Y. MINORU et al., (Yakugaku Zasshi 96/9, 1094–102, 1976).

The following non-restrictive Examples illustrate the invention:

EXAMPLE 1

3-Methyl-5-oxo-7-(3-pyridyl)-triazolo-[4,3-a]pyrimidine (1H) (X=3-pyridyl, $R_1$=H, $R_2$=$CH_3$) (derivative no. 1)

23 g (0.113 mol) of 2-hydrazino-4-oxo-6-(3-pyridyl)-pyrimidine (compound of formula II) and 73.6 g of ethyl orthoacetate and 500 ml of n-butanol are mixed in an erlenmeyer flask. The mixture is refluxed for 4 hours and then filtered and the precipitate is washed with ether.

24 g of crystals are recovered (yield 93%).
TLC ethyl acetate/methanol (90:10)
Melting point 260° C.

EXAMPLE 2

3-Methyl-5-oxo-7-(2-pyridyl)-triazolo[4,3-a]pyrimidine (1H) (X=2-pyridyl, $R_1$=H, $R_2$=$CH_3$) (derivative no. 2)

Using the method described in Example 1, this compound is prepared from 2-hydrazino-4-oxo-6-(2-pyridyl)-pyrimidine and ethyl orthoacetate by heating for 4 hours to 95° C. White crystals are obtained (yield 91%).

Melting point 260° C.

EXAMPLE 3

3-Methyl 5-oxo-7-(4-pyridyl)-triazolo-[4,3-a]pyrimidine (1H) (X=4-pyridyl, $R_1$=H, $R_2$=$CH_3$) (derivative no. 3)

Using the same procedure as in Example 1, this compound is prepared from 2-hydrazino-4-oxo-6-(4-pyridyl)-pyrimidine and ethyl orthoacetate by refluxing for 3 hours. Light yellow crystals are obtained (yield 83%).

Melting point 260° C.

EXAMPLE 4

3-Ethyl-5-oxo-7-(2-pyridyl)-triazolo-[4,3-a]pyrimidine (1H) (X=2-pyridyl, $R_1$=H, $R_2$=$CH_2$—$CH_3$) (derivative no. 4)

Using the same procedure as in Example 1, this compound is prepared from 2-hydrazino-4-oxo-6-(2-pyridyl)-pyrimidine, melting point 250° C., and ethyl orthopropionate by refluxing for 2 hours. White crystals are obtained (yield 85%).

Melting point 260° C.

EXAMPLE 5

3-Ethyl-5-oxo-7-(3-pyridyl)-triazolo[4,3-a]pyrimidine (1H) (X=3-pyridyl, $R_1$=H, $R_2$=$CH_2$—$CH_3$) (derivative no. 5)

Using the same procedure as in Example 1, this compound is prepared from 2-hydrazino-4-oxo-6-(3-pyridyl)-pyrimidine and ethyl orthopropionate by refluxing for 2 hours. Light yellow crystals are obtained (yield 63%).

Melting point 260° C.

EXAMPLE 6

3-Ethyl-5-oxo-7-(4-pyridyl)-triazolo[4,3-a]pyrimidine (1H) (X=4-pyridyl, $R_1$=H, $R_2$=$CH_2$—$CH_3$) (derivative no. 6)

Using the same procedure as in Example 1, this compound is prepared from 2-hydrazino-4-oxo-6-(4-pyridyl)-pyrimidine and ethyl orthopropionate by refluxing for 2 hours. Beige crystals are obtained (yield 42%).

Melting point 260° C.

EXAMPLE 7

1-Ethyl-3-methyl-5-oxo-7-(3-pyridyl)-triazolo[4,3-a]pyrimidine (X=3-pyridyl, $R_1$=$CH_2$—$CH_3$, $R_2$=$CH_3$) (derivative no. 7)

A solution of 6.4 g (0.028 mol) of 3-methyl-5-oxo-7-(3-pyridyl)-triazolo[4,3-a]pyrimidine (1H) (derivative no. 1) in 400 ml of DMF is added dropwise to a flask containing 1.36 g (0.028 mol) of 50% sodium hydride suspended in 50 ml of dimethylformamide (DMF) under a nitrogen atmosphere. When the release of hydrogen has ended, the mixture is heated to 70° C. and 2.2 ml (0.028 mol) of ethyl bromide are added slowly, whilst the mixture is kept at this temperature for 2 hours. The DMF is eliminated and the residue is taken up in water and then extracted with ethyl acetate. The organic solution is then dried over magnesium sulphate and concentrated and recrystallised from heptane.

White fluffy crystals are obtained (yield 69%).
TLC ethyl acetate.
Melting point: 144° C.

In order to obtain the methanesulphonate, 5 g (0.0196 mol) of the compound obtained, 20 ml of water and 1.88 g (0.0196 mol) of methanesulphonic acid are mixed together. By lyophilisation of the solution, a powder is obtained which, after being washed with ether, is dried in vacuo.

6.9 g of a white powder are obtained (yield 98.5%). The salt obtained is recrystallised with half a molecule of water and its melting point is 208° C.

EXAMPLE 8

1-Ethyl-3-methyl-5-oxo-7-(2-pyridyl)-triazolo-[4,3-a]-pyrimidine (X=2-pyridyl, $R_1$=$CH_2$—$CH_3$, $R_2$=$CH_3$) (derivative no. 8)

Using the same procedure as in Example 7, this compound is prepared from 3-methyl-5-oxo-7-(2-pyridyl)-triazolo[4,3-a]pyrimidine (1H) and ethyl bromide. Orange fluffy crystals are obtained (yield 72%).

Melting point: 156° C.

EXAMPLE 9

1-Ethyl-3-methyl-5-oxo-7-(4-pyridyl)-triazolo[4,3-a]pyrimidine (X=4-pyridyl, $R_1$=$CH_2$—$CH_3$, $R_2$=$CH_3$) (derivative no. 9)

Using the procedure described in Example 7, this compound is prepared from 3-methyl-5-oxo-7-(4-pyridyl)-triazolo[4,3-a]pyrimidine (1H) and ethyl bromide.

Whitish crystals are obtained (53%)
Melting point: 160° C.–162° C.

EXAMPLE 10

1-Methyl-3-methyl-5-oxo-7-(2-pyridyl)-triazolo[4,3-a]pyrimidine (X=2-pyridyl, $R_1$=$CH_3$, $R_2$=$CH_3$) (derivative no. 10)

Using the procedure described in Example 7, this compound is prepared from 3-methyl-5-oxo-7-(2-pyridyl)-triazolo[4,3-a]pyrimidine (1H) and methyl iodide. White crystals are obtained (yield 81%).

Melting point: 211° C.

EXAMPLE 11

1-Methyl-3-methyl-5-oxo-7-(4-pyridyl)-triazolo[4,3-a]pyrimidine (X=4-pyridyl, $R_1$=$CH_3$, $R_2$=$CH_3$) (derivative no. 11)

Using the procedure described in Example 7, this compound is prepared from 3-methyl-5-oxo-7-(4-pyridyl)-triazolo[4,3-a]pyrimidine (1H) and methyl iodide.

Beige crystals are obtained (yield 50%)
Melting point: 200° C.–202° C.

EXAMPLE 12

1-Propyl-3-methyl-5-oxo-7-(2-pyridyl)-triazolo[4,3-a]pyrimidine (X=2-pyridyl, $R_1$=$CH_2$—$CH_2$—$CH_3$, $R_2$=$CH_3$) (derivative no. 12)

Using the procedure described in Example 7, this compound is prepared from 3-methyl-5-oxo-7-(2-pyridyl)-triazolo[4,3-a]pyrimidine [1H] and propyl iodide. White crystals are obtained (yield 80%).

Melting point: 124° C.

EXAMPLE 13

1-Methyl-3-ethyl-5-oxo-7-(2-pyridyl)-triazolo[4,3-a]pyrimidine (X=2-pyridyl, $R_1$=$CH_3$, $R_2$=$CH_2$—$CH_3$) (derivative no. 13)

Using the same procedure as in Example 7, this compound is prepared from 3-ethyl-5-oxo-(2-pyridyl)-7-triazolo[4,3-a]pyrimidine [1H] and methyl iodide.

White crystals are obtained (yield 70%).
Melting point: 172° C.

EXAMPLE 14

1-Propyl-3-ethyl-5-oxo-7-(2-pyridyl)-triazolo[4,3-a]pyrimidine (X=2-pyridyl, $R_1$=$CH_2$—$CH_2$—$CH_3$, $R_2$=$CH_2$—$CH_3$) (derivative no. 14)

Using the procedure described in Example 7 this compound is prepared from 3-ethyl-5-oxo-7-(2-pyridyl)-triazolo[4,3-a]pyrimidine [1H] and propyl iodide.

White crystals are obtained (yield 85%).
Melting point: 153° C.

EXAMPLE 15

1-Ethyl-3-methyl-5-oxo-7-(5-butyl-2-pyridyl)-triazolo[4,3-a]pyrimidine (X=5-butyl-2-pyridyl, $R_1=CH_2-CH_3$, $R_2=CH_3$) (derivative no. 15)

Using the procedure described in Example 7, this compound is prepared from 3-methyl-5-oxo-7-(5-butyl-2-pyridyl)-thiazolo[4,3-a]pyrimidine [1H] and ethyl bromide.

White crystals are obtained (yield 82%).
Melting point: 106° C.

EXAMPLE 16

1-Methyl-3-methyl-5-oxo-(3-pyridyl)-7-triazolo[4,3-a]pyrimidine methane sulphonate (X=3-pyridyl, $R_1=CH_3$, $R_2=CH_3$) (derivative no. 16)

Using the same procedure as in Example 7, this compound is prepared from 3-methyl-5-oxo-7-(3-pyridyl)-triazolo[4,3-a]pyrimidine [1H] and methyl iodide. The salt is then prepared using methanesulphonic acid.

Whitish crystals are obtained (yield 62%).
Melting point of the base: 208° C.

EXAMPLE 17

1-Propyl-3-methyl-5-oxo-7-(3-pyridyl)-triazolo[4,3-a]pyrimidine methane sulphonate (X=3-pyridyl, $R_1=CH_2-CH_2-CH_3$, $R_2=CH_3$) (derivative no. 17)

Using the same procedure as in Example 7, this compound is prepared from 3-methyl-5-oxo-7-(3-pyridyl)-triazolo[4,3-a]pyrimidine [1H] and propyl bromide. The salt is then prepared using methane sulphonic acid.
White crystals are obtained (yield 73%).
Melting point: 108° C.

EXAMPLE 18

1-Pentyl-3-methyl-5-oxo-(3-pyridyl)-7-triazolo[4,7-3-a]pyrimidine (X=3-pyridyl, $R_1=(CH_2)_4-CH_3$, $R_2=CH_3$) (derivative no. 18)

Using the same procedure as in Example 7 this compound is prepared from 3-methyl-5-oxo-7-(3-pyridyl)-triazolo[4,3-a]pyrimidine [1H] and pentyl bromide.

White crystals are obtained (yield 83%).
Melting point: 97° C.

EXAMPLE 19

1-Ethyl-3-butyl-5-oxo-7-(3-pyridyl)-triazolo[4,3-a]pyrimidine (X=3-pyridyl, $R_1=CH_2-CH_3$, $R_2=(CH_2)_3-CH_3$) (derivative no. 19)

Using the procedure used in Example 7, this compound is prepared from 3-butyl-5-oxo-7-(3-pyridyl)-triazolo[4,3-a]pyrimidine [1H] and ethyl bromide.

Cream crystals are obtained (yield 35%).
Melting point: 119° C.

EXAMPLE 20

3-Butyl-5-oxo-7-(3-pyridyl)-triazolo[4,3-a]pyrimidine [1H] (X=3-pyridyl, $R_1=H$, $R_2=(CH_2)_3CH_3$) (derivative no. 20)

Using the procedure used in Example 1 this compound is prepared from 2-hydrazino-4-oxo-(3-pyridyl)-pyrimidine and methyl orthovalerate.

White crystals are obtained (yield 76%).
Melting point: 250° C.

EXAMPLE 21

1-Methyl-3-butyl-5-oxo-7-(3-pyridyl)-triazolo[4,3-a]pyrimidine (X=3-pyridyl, $R_1=CH_3$, $R_2=(CH_2)_3-CH_3$) (derivative no. 21)

Using the procedure described in Example 7, this compound is prepared from 3-butyl-5-oxo-7-(3-pyridyl)-7-triazolo[4,3-a]pyrimidine [1H] and methyl iodide.

White crystals are obtained (yield 74%).
Melting point: 124° C.

EXAMPLE 22

1-Propyl-3-methyl-5-oxo-7-(4-pyridyl)-triazolo[4,3-a]pyrimidine (X=4-pyridyl, $R_1=CH_2-CH_2-CH_3$, $R_2=CH_3$) (derivative no. 22)

Using the procedure described in Example 7 this compound is prepared from 3-methyl-5-oxo-7-(4-pyridyl)-triazolo[4,3-a]pyrimidine [1H] and propyl bromide.

White crystals are obtained (yield 58%).
Melting point: 144° C.

EXAMPLE 23

1-(2-Propyl)-3-methyl-5-oxo-7-(4-pyridyl)-triazolo[4,3-a]pyrimidine (X=4-pyridyl, $R_1=(CH_3)_2-CH$, $R_2=CH_3$ (derivative no. 23)

Using the procedure described in Example 7 this compound is prepared from 3-methyl-5-oxo-7-(4-pyridyl)-triazolo[4,3-a]pyrimidine[1H] and isopropyl chloride.

White crystals are obtained (yield 32%).
Melting point: 170° C.

EXAMPLE 24

1-Butyl-3-methyl-5-oxo-7-(4-pyridyl)-triazolo[4,3-a]pyrimidine (X=4-pyridyl, $R_1=(CH_2)_3-CH_3$, $R_2=CH_3$) (derivative no. 24)

Using the procedure described in Example 7 this compound is prepared from 3-methyl-5-oxo-7-(4-pyridyl)-triazolo[4,3-a]pyrimidine[1H] and butyl bromide.

White crystals are obtained (yield 85%).
Melting point: 106° C.

EXAMPLE 25

1-(2-Propynyl)-3-methyl-5-oxo-7-(4-pyridyl)-triazolo[4,3-a]pyrimidine[1(x=4-pyridyl, $R_1=CH_2-C\equiv CH$, $R_2=CH_3$ (derivative no. 25)

Using the same procedure as in Example 7 this compound is prepared from 3-methyl-5-oxo-7-(4-pyridyl)-triazolo[4,3-a]pyrimidine[1H] and propargyl bromide.

White crystals are obtained (yield 28%).
Melting point: 178° C.

EXAMPLE 26

1-Allyl-3-methyl-5-oxo-7-(4-pyridyl)-triazolo[4,3-a]pyrimidine (X=4-pyridyl, $R_1=CH_2-CH=CH_2$, $R_2=CH_3$) (derivative no. 26)

Using the procedure described in Example 7 this compound is prepared from 3-methyl-5-oxo-7-(4-pyridyl)-triazolo[4,3-a]pyrimidine[1H] and allyl bromide.

Whitish crystals are obtained (yield 47%).
Melting point: 146° C.

EXAMPLE 27

1-Methyl-3-ethyl-5-oxo-7-(4-pyridyl)-triazolo[4,3-a]pyrimidine methane sulphonate (X=4-pyridyl, $R_1$=$CH_3$, $R_2$=$CH_2$—$CH_3$) (derivative no. 27)

Using the procedure described in Example 7 this compound is prepared from 3-ethyl-5-oxo-7-(4-pyridyl)-triazolo[4,3-a]pyrimidine[1H] and methyl iodide. The salt is then prepared using methanesulphonic acid. White crystals are obtained (yield 65%).

Melting point: 190° C.

EXAMPLE 28

1,3-Diethyl-5-oxo-7-(4-pyridyl)-triazolo[4,3-a]pyrimidine (X=4-pyridyl, $R_1$=$CH_2$—$CH_3$, $R_2$=$CH_2$—$CH_3$) (derivative no. 28)

Using the procedure described in Example 7 this compound is prepared from 3-ethyl-5-oxo-7-(4-pyridyl)-triazolo[4,3-a]pyrimidine[1H] and ethyl bromide.

White crystals are obtained (yield 81%)

Melting point: 162° C.

EXAMPLE 29

1-Propyl-3-ethyl-5-oxo-7-(4-pyridyl)-triazolo[4,3-a]pyrimidine, methane sulphonate (X=4-pyridyl, $R_1$=$CH_2$—$CH_2$—$CH_3$, $R_2$=$CH_2$—$CH_3$) (derivative no. 29)

Using the procedure described in Example 7 this compound is prepared from 3-ethyl-5-oxo-7-(4-pyridyl)-triazolo[4,3-a]pyrimidine[1H] and propyl bromide.

Beige crystals are obtained (yield 59%).

Melting point: 110° C.

The results of the toxicological and pharmacological tests reported hereinafter demonstrated the valuable properties of the derivatives of the invention, notably their low toxicity, excellent tolerance and their cardiotonic activity.

The invention therefore also relates to a pharmaceutical composition having, in particular, a cardiotonic activity, characterised in that it contains as active principle a derivative of formula I.

TOXICOLOGICAL STUDY

The compounds of the invention are extremely well tolerated and have a low toxicity. In the course of tests of acute, chronic, sub-chronic or delayed toxicity carried out on different animal species (mice, rats and rabbits), the derivatives of the invention were well tolerated; it was not possible to find any anomaly or disturbance of any kind in the biochemical, microscopic or macroscopic tests carried out during or after the experiments.

PHARMACOLOGICAL STUDY

The cardiotonic activity of the medicament of the invention was demonstrated by a study of the positive inotropic effect produced by the compounds of the invention. This study was carried out using the method of J. V. LEVY (Methods in Pharmacology, Volume 1, SCHWARTZ).

On albino guinea-pigs (DUNKIN-HARTLEY), both male and female, weighing from 600 g to 800 g, after the cervical vertebrae have been broken and the thorax has been opened and the pericardium torn out, the right auricle is rapidly taken and placed in a nutrient bath.

The product to be tested is added to the organ bath, which has a capacity of 50 ml, in a volume of 0.5 ml after being solubilised in 1N hydrochloric acid. The final pH of the nutrient solution is taken at the end of each experiment.

The following parameters are recorded on a polygraph:

the tension produced (isometric myograph)

the rate of contraction and the rate of relaxation calculated by the derivative of the tension in relation to time.

The frequency of the contractions is also determined from the tension curve obtained.

The effects of the derivatives being tested were researched at dosages ranging from $10^{-7}$ to $10^{-3}$ mol/liter (M/L).

The results assembled in the tables which follow relate to the most active compounds.

It is found that:

the tension produced is increased progressively from $10^{-6}$ M/L with a peak effect at $2.10^{-3}$ M/L (+197%) for compound of Example no. 7, $10^{-3}$ M/L (+129%) for compound of Example no. 9, derivative no. 12 (145%), compound of Example no. 16 (130%), compound of Example no. 17 (110%) and compound of Example No. 27 (114%).

the frequency of the contractions is not altered by the different dosages tested, the rates of contraction and relaxation follow the course of the tension produced.

The total duration of all the effects is 30 minutes.

The toxicological and pharmacological studies reported above demonstrated the low toxicity of the compounds of the invention and their good tolerance together with their valuable cardiotonic activity which makes them very useful for human and veterinary therapy.

Each single dose advantageously contains from 0.050 g to 1.00 g of active principle, whilst the dosages which can be administered per day may vary from 0.050 g to 3.00 g of active principle, depending on the age of the patient and the seriousness of the complaint being treated.

Some pharmaceutical formulations of the medicament of the invention will now be given as non-restrictive examples.

(1) Coated tablets

Compound of Example no. 5 0.200 g

Excipient: starch, officinal white sugar, calcium carbonate, talc, magnesium stearate, gum arabic, carnauba wax.

(2) Tablets

Compound of Example no. 2 0.250 g

Excipient: erythrosine, gum tragacanth, corn starch, talc, lactose and icing sugar.

The pharmaceutical composition of the invention may be presented, for oral administration, in the form of plain or coated tablets, capsules, drops, granules or syrups. It may also be presented in the form of suppositories for rectal administration and in the form of an injectable solution for parenteral administration.

| Dosages in M/L | Tension produced | Frequency of contractions | Contraction d tension d time | Relaxation d tension d time |
|---|---|---|---|---|
| Compound of Example no. 7 | | | | |
| $10^{-7}$ | 0% | 0% | 0% | 0% |
| $10^{-6}$ | 5% | 0% | 4% | 16% |
| $4 \times 10^{-6}$ | 7% | 0% | 3% | 11% |
| $4 \times 10^{-5}$ | 25% | 1% | 31% | 24% |
| $4 \times 10^{-4}$ | 76% | 5% | 80% | 69% |
| $2 \times 10^{-3}$ | 197% | 3% | 220% | 154% |
| Compound of Example no. 9 | | | | |
| $10^{-6}$ | 9% | 0% | 13% | 10% |
| $10^{-5}$ | 24% | 1% | 20% | 28% |
| $5 \times 10^{-5}$ | 26% | 3% | 29% | 36% |
| $10^{-4}$ | 59% | 4% | 51% | 64% |
| $5 \times 10^{-4}$ | 86% | 4% | 67% | 53% |
| $10^{-3}$ | 129% | 4% | 107% | 128% |
| Compound of Example no. 12 | | | | |
| $10^{-6}$ | 4% | 0% | 2% | 4% |
| $10^{-5}$ | 27% | 19% | 33% | 34% |
| $10^{-4}$ | 48% | 6% | 55% | 43% |
| $5 \times 10^{-4}$ | 73% | 17% | 70% | 48% |
| $10^{-3}$ | 145% | 19% | 153% | 140% |
| Compound of Example no. 16 | | | | |
| $10^{-6}$ | −2% | 0% | 10% | 0% |
| $10^{-5}$ | 0% | 0% | 0% | 7% |
| $10^{-4}$ | 39% | 5% | 28% | 31% |
| $5 \times 10^{-4}$ | 43% | 13% | 43% | 52% |
| $10^{-3}$ | 130% | 4% | 136% | 119% |
| Compound of Example no. 17 | | | | |
| $10^{-6}$ | 9% | 2% | 16% | 13% |
| $10^{-5}$ | 27% | 6% | 26% | 27% |
| $10^{-4}$ | 45% | 10% | 35% | 46% |
| $5 \times 10^{-4}$ | 67% | 14% | 63% | 45% |
| $10^{-3}$ | 110% | 6% | 108% | 114% |
| Compound of Example no. 27 | | | | |
| $10^{-6}$ | −3% | 4% | 0% | 0% |
| $10^{-5}$ | 10% | 8% | 18% | 10% |
| $10^{-4}$ | 32% | 17% | 31% | 48% |
| $10^{-3}$ | 114% | 27% | 103% | 104% |

(3) Gelatine capsules
Compound of Example no. 11 0.500 g
Excipient: talc, stearic acid, magnesium stearate.
(4) Suppositories
Compound of Example no. 12 0.200 g
Semi-synthetic triglycerides q.s. ad 1 suppository.
(5) Injectable solution
Compound of Example no. 6 0.250 g
Isotonic solvent q.s. ad 2 ml.

Being endowed with a positive inotropic effect, the medicament according to the invention has a valuable cardiotonic activity.

It is used to advantage in adults and children for acute cardiac insufficiency and for paroxysms of cardiac insufficiency, in certain problems of heart rhythm with a risk of imminent decompensation, in heart failure and in congestive cardiac insufficiency.

We claim:

1. Triazolo pyrimidine compounds of the formula:

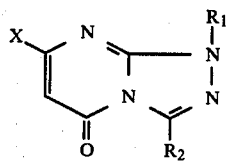

wherein X represents a pyridyl nucleus or a pyridyl nucleus substituted by a straight-chained or branched $C_{1-4}$ alkoxy or alkyl group or a hydroxy or cyano group, $R_1$ represents hydrogen or straight-chained or branched saturated or unsaturated $C_{1-5}$ aliphatic group and $R_2$ represents a straight-chained or branched $C_{1-4}$ alkyl group, and the pharmaceutically acceptable acid addition salts thereof with inorganic or organic acids.

2. A compound as claimed in claim 1, wherein said pyridyl nucleus is a 2-pyridyl, 3-pyridyl or 4-pyridyl nucleus.

3. 1-Ethyl-3-methyl-5-oxo-7-(3-pyridyl)-triazolo[4,3-a]pyrimidine.

4. 1-Ethyl-3-methyl-5-oxo-7-(4-pyridyl)-triazolo-[4,3-a]pyrimidine.

5. A cardiotonic composition for increasing cardiac contractility comprising a pharmaceutically acceptable carrier and as the active component a compound of claim 1.

6. The composition as claimed in claim 5, in a form suitable for oral, parenteral or rectal administration.

7. The composition as claimed in claim 5, in the form of dosage units each containing from 0.050 g to 1.00 g.

8. A cardiotonic composition for increasing cardiac contractility comprising a pharmaceutically acceptable carrier and as the active component a compound of claim 2.

9. A cardiotonic composition for increasing cardiac contractility comprising a pharmaceutically acceptable carrier and as the active component a compound of claim 3.

10. A cardiotonic composition for increasing cardiac contractility comprising a pharmaceutically acceptable carrier and as the active component a compound of claim 4.

11. The method for increasing cardiac contractility in a patient requiring such treatment which comprises administering in an effective amount the composition of claim 5.

12. The method for increasing cardiac contractility in a patient requiring such treatment which comprises administering in an effective amount the composition of claim 8.

13. The method for increasing cardiac contractility in a patient requiring such treatment which comprises administering in an effective amount the composition of claim 9.

14. The method for increasing cardiac contractility in a patient requiring such treatment which comprises administering in an effective amount the composition of claim 10.

* * * * *